United States Patent [19]

Ho et al.

[11] Patent Number: 4,894,178

[45] Date of Patent: Jan. 16, 1990

[54] ABSORBENT COMPOSITION CONTAINING SEVERELY-HINDERED AMINE MIXTURE FOR THE ABSORPTION OF $H_2S$

[75] Inventors: W. S. Winston Ho, Annandale; Eugene L. Stogryn, Edison; Guido Sartori, Annandale, all of N.J.

[73] Assignee: Exxon Research and Engineering Company, Florham Park, N.J.

[21] Appl. No.: 106,796

[22] Filed: Oct. 13, 1987

[51] Int. Cl.$^4$ ............................................. C09K 3/00
[52] U.S. Cl. ............................. 252/189; 252/190; 252/191
[58] Field of Search ........................... 252/189, 190, 191

[56] References Cited

U.S. PATENT DOCUMENTS

| | | | |
|---|---|---|---|
| 2,722,500 | 11/1955 | Rippie et al. | 208/289 |
| 2,946,652 | 7/1960 | Block | 423/229 |
| 3,139,324 | 6/1964 | Housset | 423/229 |
| 3,535,260 | 10/1970 | Singh | 252/189 |
| 3,653,810 | 4/1972 | Bratzler et al. | 423/229 |
| 3,848,057 | 11/1974 | Leder et al. | 423/223 |
| 4,080,423 | 3/1978 | Smith et al. | 423/226 |
| 4,112,052 | 9/1978 | Sartori et al. | 423/228 |
| 4,153,674 | 5/1979 | Verloop et al. | 423/573 R |
| 4,240,922 | 12/1980 | Sartori et al. | 252/189 |
| 4,336,233 | 6/1982 | Appl et al. | 423/228 |
| 4,405,580 | 9/1983 | Stogryn et al. | 423/226 |
| 4,405,581 | 9/1983 | Savage et al. | 423/226 |
| 4,405,583 | 9/1983 | Stogryn et al. | 423/228 |
| 4,405,585 | 9/1983 | Sartori et al. | 423/228 |
| 4,471,138 | 9/1984 | Stogryn | 564/508 |
| 4,487,967 | 12/1984 | Stogryn et al. | 564/474 |
| 4,578,517 | 3/1986 | Johnson et al. | 564/479 |
| 4,618,481 | 10/1986 | Heinzelmann et al. | 423/228 |
| 4,665,195 | 5/1987 | Stogryn et al. | 548/523 |

FOREIGN PATENT DOCUMENTS 0134948 3/1985 European Pat. Off. .
2017524 10/1979 United Kingdom .

OTHER PUBLICATIONS

DeLos F. Detar, "Effects of Alkyl Groups on Rates of $S_N2$ Reactions", J. Org. Chem 1980, 45 5174–5176.
DeLos F. Detar, "Effects of Alkyl Groups on Rates of Acyl-Transfer Reactions", J. Org. Chem, 1980, 45, 5166–5174.

*Primary Examiner*—Catherine S. Kilby Scalzo
*Attorney, Agent, or Firm*—Ronald D. Hantman

[57] ABSTRACT

The present invention relates to a mixture of severely-hindered amines, such as bis-(tertiarybutylaminoethoxy)-ethane (BTEE) and ethoxyethoxyethanoltertiarybutylamine (EEETB), and a one-step synthesis method for its preparation. Besides, this invention describes the use of the mixture for the removal of $H_2S$, especially the selective removal of $H_2S$ in the presence of $CO_2$.

4 Claims, 8 Drawing Sheets

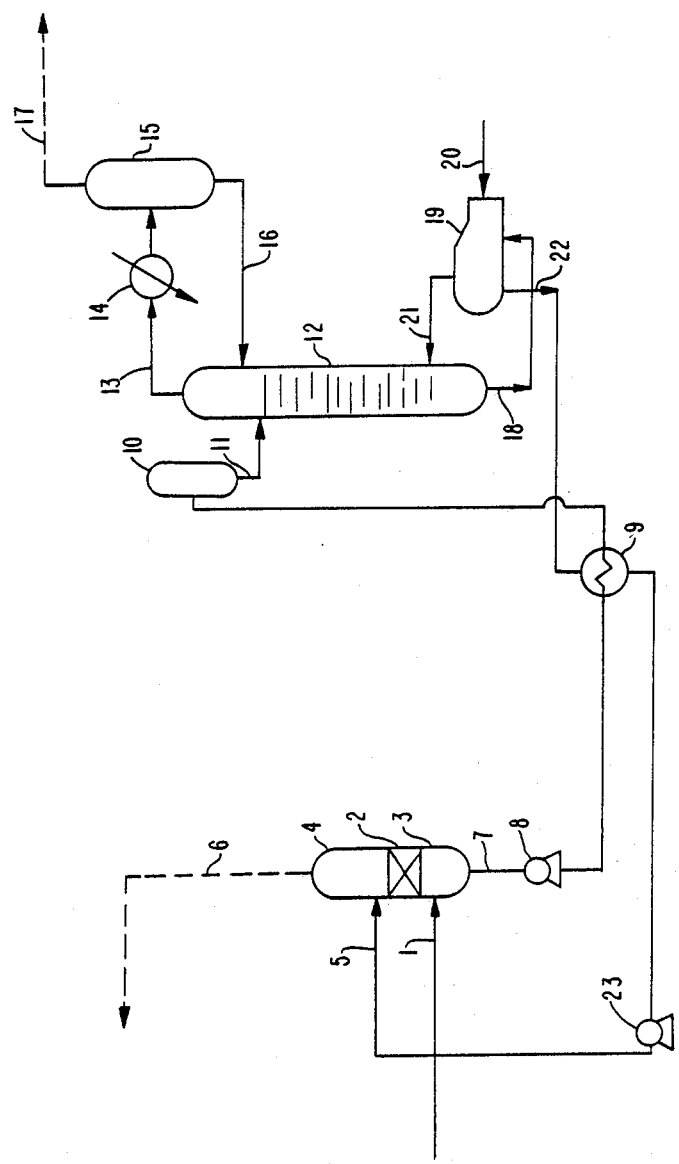
F I G. 1

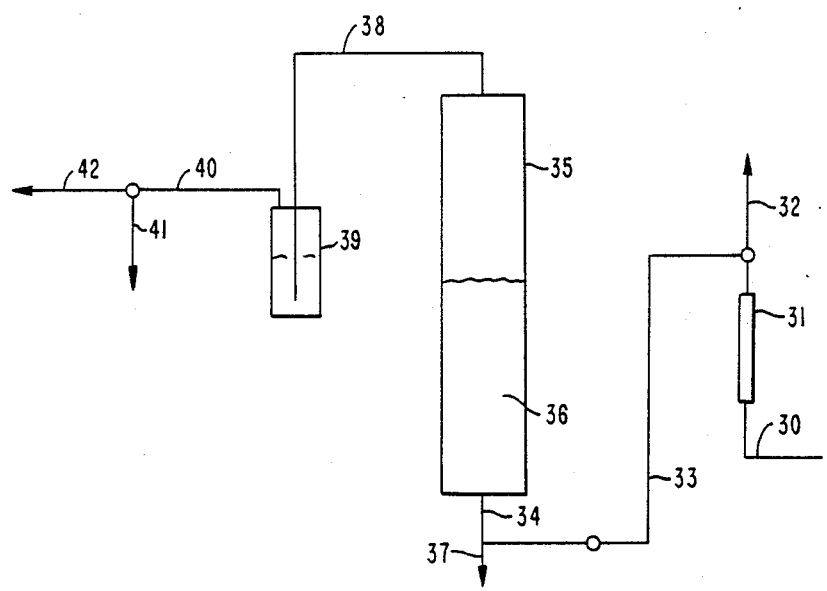
F I G. 2

ABSORBENT COMPOSITION CONTAINING SEVERELY-HINDERED AMINE MIXTURE FOR THE ABSORPTION OF H₂S

FIELD OF THE INVENTION

The present invention relates to a mixture of severely-hindered amines, such as bis-(tertiarybutylaminoethoxy)-ethane (BTEE) and ethoxyethoxyethanol-tertiarybutylamine (EEETB), and a one-step synthesis method for its preparation. Besides, this invention describes the use of the mixture for the removal of $H_2S$, especially the selective removal of $H_2S$ in the presence of $CO_2$.

BACKGROUND OF THE INVENTION

It is well known in the art to treat gases and liquids, such as mixtures containing acidic gases including $CO_2$, $H_2S$, $CS_2$, HCN, COS and oxygen and sulfur derivatives of $C_1$ to $C_4$ hydrocarbons with amine solutions to remove these acidic gases. The amine usually contacts the acidic gases and the liquids as an aqueous solution containing the amine in an absorber tower with the aqueous amine solution contacting the acidic fluid countercurrently.

The treatment of acid gas mixtures containing, inter alia, $CO_2$ and $H_2S$ with amine solutions typically results in the simultaneous removal of substantial amounts of both the $CO_2$ and $H_2S$. For example, in one such process generally referred to as the "aqueous amine process," relatively concentrated amine solutions are employed. A recent improvement on this process involves the use of sterically hindered amines as described in U.S. Pat. No. 4,112,052, to obtain nearly complete removal of acid gases such as $CO_2$ and $H_2S$. This type of process may be used where the partial pressures of the $CO_2$ and related gases are low. Another process, often used for specialized applications where the partial pressure of $CO_2$ is extremely high and/or where many acid gases are present, e.g., $H_2S$, COS, $CH_3SH$, and $CS_2$, involves the use of an amine in combination with a physical absorbent, generally referred to as the "non-aqueous solvent process." An improvement on this process involves the use of sterically hindered amines and organic solvents as the physical absorbent such as described in U.S. Pat. No. 4,112,051.

It is often desirable, however, to treat acid gas mixtures containing both $CO_2$ and $H_2S$ so as to remove the $H_2S$ selectively from the mixture, thereby minimizing removal of the $CO_2$. Selective removal of $H_2S$ results in a relatively high $H_2S/CO_2$ ratio in the separated acid gas which simplifies the conversion of $H_2S$ to elemental sulfur using the Claus process.

The typical reactions of aqueous secondary and tertiary amines with $CO_2$ and $H_2S$ can be represented as follows:

   (1)

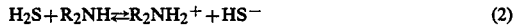   (2)

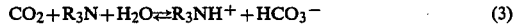   (3)

   (4)

wherein R is an organic radical which may be the same or different and may be substituted with a hydroxyl group. The above reactions are reversible, and the partial pressures of both $CO_2$ and $H_2S$ are thus important in determining the degree to which the above reactions occur.

While selective $H_2S$ removal is applicable to a number of gas treating operations including treatment of hydrocarbon gases from shale pyrolysis, refinery gas and natural gas having a low $H_2S/CO_2$ ratio, it is particularly desirable in the treatment of gases wherein the partial pressure of $H_2S$ is relatively low compared to that of $CO_2$ because the capacity of an amine to absorb $H_2S$ from the latter type gases is very low. Examples of gases with relatively low partial pressures of $H_2S$ include synthetic gases made by coal gasification, sulfur plant tail gas and low-Joule fuel gases encountered in refineries where heavy residual oil is being thermally converted to lower molecular weight liquids and gases.

Although it is known that solutions of primary and secondary amines such as monoethanolamine (MEA), diethanolamine (DEA), dipropanolamine (DPA), and hydroxyethoxyethylamine (DGA) absorb both $H_2S$ and $CO_2$ gas, they have not proven especially satisfactory for preferential absorption of $H_2S$ to the exclusion of $CO_2$ because the amines undergo a facile reaction with $CO_2$ to form carbamates.

Diisopropanolamine (DIPA) is relatively unique among secondary aminoalcohols in that it has been used industrially, alone or with a physical solvent such as sulfolane, for selective removal of $H_2S$ from gases containing $H_2S$ and $CO_2$, but contact times must be kept relatively short to take advantage of the faster reaction of $H_2S$ with the amine compared to the rate of $CO_2$ reaction as shown in Equations 2 and 4 hereinabove.

In 1950, Frazier and Kohl, Ind. and Eng. Chem. 42, 2288 (1950) showed that the tertiary amine, methyldiethanolamine (MDEA), has a high degree of selectivity toward $H_2S$ absorption over $CO_2$. This greater selectivity was attributed to the relatively slow chemical reaction of $CO_2$ with tertiary amines as compared to the rapid chemical reaction of $H_2S$. The commercial usefulness of MDEA, however, is limited because of its restricted capacity for $H_2S$ loading and its limited ability to reduce the $H_2S$ content to the level at low pressures which is necessary for treating, for example, synthetic gases made by coal gasification.

U.K. Patent Publication 2,017,524A to Shell disclosed that aqueous solutions of dialkylmonoalkanolamines, and particularly diethylmonoethanolamine (DEAE), have higher selectivity and capacity for $H_2S$ removal at higher loading levels than MDEA solutions. Nevertheless, even DEAE is not very effective for the low $H_2S$ loading frequently encountered in the industry. Also, DEAE has a boiling point of 161° C. and as such, it is characterized as being a low-boiling, relatively highly volatile amino alcohol. Such high volatilities under most gas scrubbing conditions result in large material losses with consequent losses in economic advantages.

U.S. Pat. Nos. 4,405,581; 4,405,583 and 4,405,585 to Exxon Research and Engineering Company disclose the use of severely sterically hindered amine compounds for the selective removal of $H_2S$ in the presence of $CO_2$. Compared to aqueous methyldiethanolamine (MDEA) severely sterically hindered amines lead to much higher selectivity at high $H_2S$ loadings.

U.S. Pat. No. 4,487,967 to Exxon Research and Engineering Company discloses a catalytic synthesis process for selectively preparing severely sterically hindered secondary aminoether alcohols by reacting a primary amino compound with a polyalkenyl ether glycol in the presence of a hydrogenation catalyst at elevated temperatures and pressures.

U.S. Pat. No. 4,665,195 to Exxon Research and Engineering Company discloses a catalytic synthesis process for producing di-amino-polyalkenyl ethers by reacting (a) one or more acyclic or heterocyclic amino compounds with (b) one or more polyalkenyl ether glycols or polyalkenyl amino ether alcohols, in the presence of a hydrogenation catalyst at elevated temperatures and pressures.

SUMMARY OF THE INVENTION

The present invention is a mixture of two severely hindered amines with the following formula:

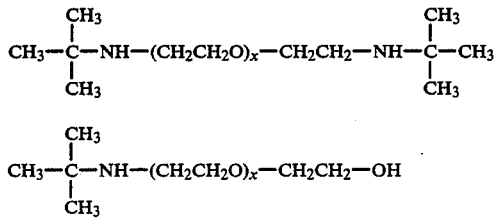

with x being an integer ranging from 2 to 6. This mixture can be prepared in the novel one-step synthesis, by the catalytic tertiarybutylamination of the polyalkenyl ether glycol, HO—(CH$_2$CH$_2$O)$_x$—CH$_2$CH$_2$—OH. For example, a mixture of bis(tertiarybutylaminoethoxy)-ethane (BTEE) and ethoxyethoxyethanol-tertiarybutylamine (EEETB) can be obtained by the catalytic tertiarybutylamination of triethylene glycol.

Another aspect of the present invention is that the severely hindered amine mixture, e.g., BTEE/EEETB, in aqueous solution can be used for the selective removal of H$_2$S in the presence of CO$_2$. The aqueous amine solution can also be used for the removal of H$_2$S from gaseous streams in which H$_2$S is the only acidic component, as is often the case in refineries.

DESCRIPTION OF THE DRAWINGS

FIG. 1 is a diagrammatic flow sheet illustrating an absorption-regeneration unit for removal of H$_2$S from gaseous streams containing H$_2$S and CO$_2$.

FIG. 2 is a diagrammatic flow sheet illustrating a sparged absorber unit for use in rapid determination of the selectivity of the amino compound for selective removal of H$_2$S from gaseous streams containing H$_2$S and CO$_2$.

DETAILED DESCRIPTION OF THE INVENTION

Figure 3:
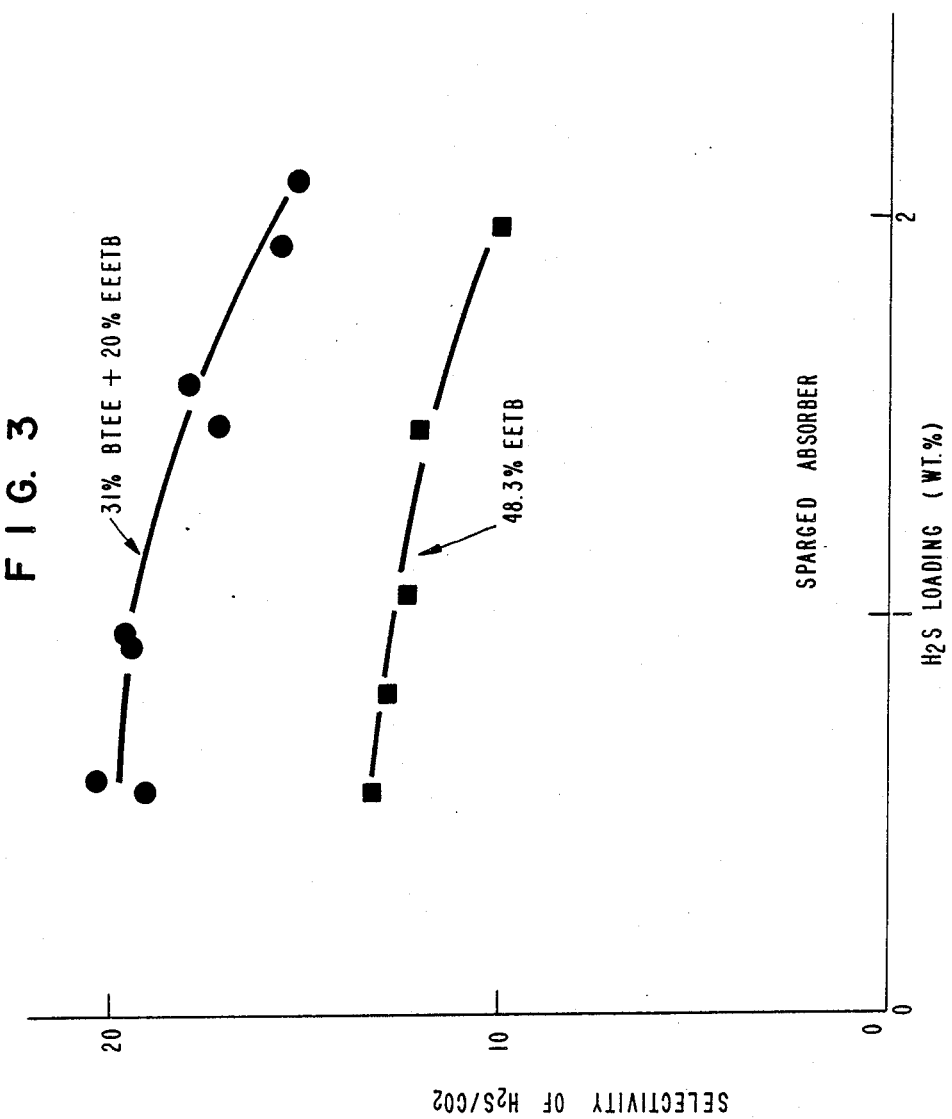
FIG. 3 shows that the selectivity of H$_2$S vs. CO$_2$ obtainable with a 31 wt % /20 wt % mixture of bis-(tertiarybutylaminoethoxy)-ethane (BTEE)/ethoxyethoxy ethanol-tertiarybutylamine (EEETB) in aqueous solution is higher than that obtainable with 48.3 wt % aqueous solution of the severely hindered ethoxyethanolter- tiarybutylamine (EETB).

The present invention includes a mixture of two severely hindered amines with the following formula:

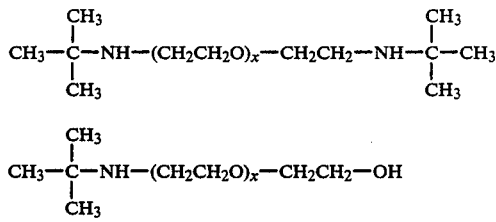

with x being an integer ranging from 2 to 6 and the weight ratio of the first amine to the second amine ranging from 0.43:1 to 2.3:1, which can be prepared in the one-step synthesis, by the catalytic tertiarybutylamination of the polyalkenyl ether glycol, HO—(CH$_2$CH$_2$O)$_x$—CH$_2$CH$_2$—OH. For example, a mixture of bis-(tertiarybutylaminoethoxy)-ethane (BTEE) and ethoxyethoxyethanol-tertiarybutylamine (EEETB) can be obtained by the catalytic tertiarybutylamination of triethylene glycol.

The catalytic amination process of the one-step synthesis hereof is carried out under pressure at a temperature ranging from about 160° to about 425° C., preferably from about 180° to about 400° C., and most preferably from about 190° to about 350° C. The pressure in the reactor may range from about 50 to about 3000 psig, preferably from about 100 to about 1000 psig, and most preferably from about 150 to about 750 psig.

The reactor used may include any suitable vessel capable of withstanding the pressures necessary to carry out the amination process. Preferably, in the amination the reactants are passed over a fixed bed of the catalyst, either concurrently or counter-currently. Other reactors suitable for use herein include moving bed reactors and continuous stirred reactors. For example, in a continuous stirred reactor the catalyst is circulated and the reactants and reaction product are passed through the reaction vessel at a controlled rate.

The hydrogenation catalyst used in the amination process herein may include any of the known hydrogenation catalysts. Illustrative hydrogenation catalysts include platinum, palladium and other noble metals such as ruthenium, rhodium, osmium and iridium deposited on inert supports such as carbon, silica, alumina or other refractory oxides, Raney nickel, nickel-on-kieselguhr, nickel on inert support, massive nickel or nickel-cobalt or nickel-cobalt-copper coprecipitated with silicate and/or aluminum salts having alumina or kieselguhr supports. Preferred catalysts include coprecipitated nickel, nickel-cobalt, and nickel-cobalt-copper supported on silica, alumina or a mixture thereof. Also preferred is platinum supported on alumina. Still more preferred are catalysts having increasing concentrations of nickel, about 40% to 70% nickel, by weight. Since preferred catalysts include those massive-metal coprecipitated hydrogenation catalysts described in U.S. Pat. Nos. 3,697,445; 4,251,394; 4,251,672; 4,263,173; 4,263,225; 4,273,680; 4,273,939; 4,307,248; 4,318,829; and the metal coprecipitated catalysts containing aluminum and silica disclosed and claimed in U.S. Ser. Nos. 388,966 and 388,967, the disclosures of which are incorporated herein by reference. It is preferred that the catalyst be reduced or activated by a reductant, such as hydrogen prior to use in the amination reaction. This reduction or activation is typically carried out by passing hydrogen over the catalyst at temperatures ranging from 175° to about 400° C., preferably 200° to about 350° C.

The concentration of the hydrogenation catalyst is that which is catalytically effective and that amount will generally range from about 0.1 to about 10 weight percent, based on the weight of the reactant charge. The normal pretreatment conditions and handling of the hydrogenation catalyst should be practiced as known to those skilled in the hydrogenation catalyst art. The mole ratio of amino compound to polyalkenyl ether glycol employed herein ranges from 1.2:1 to 4:1.

For purposes of this invention it may be desirable to include an inert solvent in the reaction medium. Preferably the solvent is a solvent such as a cyclic or linear ether or a hydrocarbon containing compound in which the reactants will dissolve. The solvent should be of relatively low molecular weight to facilitate its removal from the product of the reaction. The amount of the solvent may vary, but will generally range from about 10 to 50 wt. %, preferably from 15 to 30 wt. % based on the weight of the reactants used. Preferred solvents include tetrahydrofuran, dimethylether of ethylene glycol and toluene.

Reduction of the catalyst may be carried out in situ while conducting the process by the presence of hydrogen. Hydrogen, however, is not essential to conducting the process but is preferably employed, for example, to minimize catalyst deactivation.

Once the reaction has been completed, the reaction product mixture can be conveniently recovered by known techniques such as solvent evaporation, the evaporation of volatile components, distillation and the like.

The composition of BTEE has been disclosed in U.S. Pat. No. 4,405,583 and synthesized from tertiarybutylamine and bis-(2-chloroethoxy)-ethane. However, an aqueous BTEE solution suffered from- phase separation under regeneration conditions (about 110° C.). EEETB is disclosed as a new composition of matter in U.S. Pat. No. 4,471,138 and can be prepared from tertiarybutylamine and chloroethoxyethoxyethanol. EEETB in aqueous solution can be used for the selective removal of $H_2S$ in the presence of $CO_2$. However, the BTEE/EEETB mixture gives a better selectivity and a higher capacity for $H_2S$ than EEETB. The mixture does not have phase separation under regeneration conditions, i.e., this mixture overcomes the phase separation problem of BTEE. The BTEE/EEETB mixture also gives higher selectivities for $H_2S$ than observed with the severely sterically hindered amines, e.g. ethoxyethanol-tertiarybutylamine (EETB), described in U.S. Pat. No. 4,405,581 and 4,405,585.

The aqueous solution of BTEE/EEETB can also be used for the removal of $H_2S$ from gaseous streams in which $H_2S$ is the only acidic component, as is often the case in refineries. Compared to aqueous monoethanolamine, BTEE/EEETB has the advantage of lower volatility, no corrosivity, and higher stability.

Each of the amines of the present invention is an alkaline severely hindered amino compound having a $-E_s$ value (Taft's steric hindrance constant as calculated from the values given for primary amines in Table V of D. F. DeTar, *Journal of Organic Chemistry*, 45, 5174 (1980)) greater than 1.75.

The liquid medium in which the amine mixture is contained prior to use may be water, an organic solvent and mixtures thereof. Preferably, the liquid medium comprises water.

Suitable organic solvents include physical absorbents (as opposed to chemical absorbents) such as those described in U.S. Pat. No. 4,112,051, the teachings of which are hereby incorporated by reference and may be, for example, aliphatic acid amides, N-alkylated pyrrolidones, sulfones, sulfoxides, glycols and the mono- and di-ethers thereof. The preferred physical absorbents are sulfones, preferably sulfolane. If a mixture of solvent and water is used as the liquid medium, a typical amount of solvent may range from 0.1 to 5 moles per liter of total absorbent composition, preferably from about 0.5 to 3 moles per liter, depending upon the particular components used.

The absorbent composition of the present invention may include a wide range of additives typically employed in selective gas removal processes, such as antifoaming agents, antioxidants, corrosion inhibitors and the like in an effective amount.

Three characteristics which are of ultimate importance in determining the effectiveness of the amino compounds herein for $H_2S$ removal are "selectivity", "loading" and "capacity". The term "selectivity" as used throughout the specification is defined as the following mole ratio fraction:

$$\frac{\text{(moles of } H_2S/\text{moles of } CO_2) \text{ in liquid phase}}{\text{(moles of } H_2S/\text{moles of } CO_2) \text{ in gaseous phase}}$$

The higher this fraction, the greater the selectivity of the absorbent solution for the $H_2S$ in the gas mixture.

By the term "loading" is meant the concentration of the $H_2S$ gas physically dissolved and chemically combined in the absorbent solution as expressed in weight percent of the solution. The best amino compounds are those which exhibit good selectivity up to a relatively high loading level. The amino compounds used in the practice of the present invention typically have a "selectivity" of not substantially less than 10 at a "loading" of 0.2 wt. % $H_2S$, preferably, a "selectivity" of not substantially less than 10 at a loading of 0.4 wt. % $H_2S$ or more.

"Capacity" is defined as the moles or weight percent of $H_2S$ loaded in the absorbent solution at the end of the absorption step minus the moles or weight percent of $H_2S$ loaded in the absorbent solution at the end of the desorption step. High capacity enables one to reduce the amount of amine solution to be circulated and use less heat or steam during regeneration.

The acid gas mixture herein necessarily includes $H_2S$, and may optionally include other gases such as $CO_2$, $N_2$, $CH_4$, $H_2$, $CO$, $COS$, $HCN$, $C_2H_4$, $NH_3$, and the like. Often such gas mixtures are found in combustion gases, refinery gases, town gas, natural gas, syn gas, water gas, propane, propylene, heavy hydrocarbon gases, etc. The absorbent solution herein is particularly effective when the gaseous mixture is a gas, obtained, for example, from shale oil retort gas, coal or gasification of heavy oil with air/steam or oxygen/steam, thermal conversion of heavy residual oil to lower molecular weight liquids and gases, or in sulfur plant tail gas clean-up operations.

The absorption step of this invention generally involves contacting the gaseous stream with the absorbent solution in any suitable contacting vessel. In such processes, the normally gaseous mixture containing $H_2S$ and $CO_2$ from which the $H_2S$ is to be selectively removed may be brought into intimate contact with the absorbent solution using conventional means, such as a tower or vessel packed with, for example, rings or with sieve plates, or a bubble reactor.

In a typical mode of practicing the invention, the absorption step is conducted by feeding the normally gaseous mixture into the lower portion of the absorption tower while fresh absorbent solution is fed into the upper region of the tower. The normally gaseous mixture, freed largely from the $H_2S$, emerges from the upper portion of the tower, and the loaded absorbent solution, which contains the selectively absorbed $H_2S$, leaves the tower near or at its bottom. Preferably, the inlet temperature of the absorbent solution during the absorption step is in the range of from about 20° to about 100° C., and more preferably from 40° to about 60° C. Pressures may vary widely; acceptable pressures are between 5 and 2000 psia, preferably 20 to 1500 psia, and most preferably 25 to 1000 psia in the absorber. The contacting takes place under conditions such that the $H_2S$ is selectively absorbed by the solution. The absorption conditions and apparatus are designed so as to minimize the residence time of the liquid in the absorber to reduce $CO_2$ pickup while at the same time maintaining sufficient residence time of gas mixture with liquid to absorb a maximum amount of the $H_2S$ gas. The amount of liquid required to be circulated to obtain a given degree of $H_2S$ removal will depend on the chemical structure and basicity of the amino compounds and on the partial pressure of $H_2S$ in the feed gas. Gas mixtures with low partial pressures such as those encountered in thermal conversion processes will require less liquid under the same absorption conditions than gases with higher partial pressures such as shale oil retort gases.

A typical procedure for the selective $H_2S$ removal phase of the process comprises selectively absorbing $H_2S$ via countercurrent contact of the gaseous mixture containing $H_2S$ and $CO_2$ with the aqueous solution of the amino compounds in a column containing a plurality of trays at a low temperature, e.g., below 45° C., and at a gas velocity of at least about 0.3 ft/sec (based on "active" or aerated tray surface), depending on the operating pressure of the gas, said tray column having fewer than 20 contacting trays, with, e.g., 4–16 trays being typically employed.

After contacting the normally gaseous mixture with the absorbent solution, which becomes saturated or partially saturated with $H_2S$, the solution may be at least partially regenerated so that it may be recycled back to the absorber. As with absorption, the regeneration may take place in a single liquid phase. Regeneration or desorption of the acid gases from the absorbent solution may be accomplished by conventional means such as pressure reduction of the solution or increase of temperature to a point at which the absorbed $H_2S$ flashes off, or by passing the solution into a vessel of similar construction to that used in the absorption step, at the upper portion of the vessel, and passing an inert gas such as air or nitrogen or preferably steam upwardly through the vessel. The temperature of the solution during the regeneration step should be in the range from about 50° to about 170° C., and preferably from about 80° to 120° C., and the pressure of the solution on regeneration should range from about 0.5 to 100 psia, preferably 1 to about 50 psia. The absorbent solution, after being cleansed of at least a portion of the $H_2S$ gas, may be recycled back to the absorbing vessel. Makeup absorbent may be added a needed.

In the preferred regeneration technique, the $H_2S$-rich solution is sent to the regenerator wherein the absorbed components are stripped by the steam which is generated by reboiling the solution. Pressure in the flash drum and stripper is usually 1 to about 50 psia, preferably 15 to about 30 psia, and the temperature is typically in the range from about 50° to 170° C., preferably about 80° to 120° C. Stripper and flash temperatures will, of course, depend on stripper pressure; thus at about 15 to 30 psia stripper pressure, the temperature will be about 80° to about 120° C. during desorption. Heating of the solution to be regenerated may very suitably be effected by means of indirect heating with low-pressure steam. It is also possible, however, to use direct injection steam.

In one embodiment for practicing the entire process herein, as illustrated in FIG. 1, the gas mixture to be purified is introduced through line 1 into the lower portion of a gas-liquid countercurrent contacting column 2, said contacting column having a lower section 3 and an upper section 4. The upper and lower sections may be segregated by one or a plurality of packed beds as desired. The absorbent solution as described above is introduced into the upper portion of the column through a pipe 5. The solution flowing to the bottom of the column encounters the gas flowing countercurrently and dissolves the $H_2S$ preferentially. The gas freed from most of the $H_2S$ exits through a pipe 6 for final use. The solution, containing mainly $H_2S$ and some $CO_2$, flows toward the bottom portion of the column, from which it is discharged through pipe 7. The solution is then pumped via optional pump 8 through an optional heat exchanger and cooler 9 disposed in pipe 7, which allows the hot solution from the regenerator 12 to exchange heat with the cooler solution from the absorber column 2 for energy conservation. The solution is entered via pipe 7 to a flash drum 10 equipped with a line (not shown) which vents to line 13 and then introduced by pipe 11, into the upper portion of the regenerator 12, which is equipped with several plates and effects the desorption of the $H_2S$ and $CO_2$ gases carried along in the solution. This acid gas mixture is passed through a pipe 13 into a condenser 14 wherein cooling and condensation of water and amine solution from the gas occur. The gas then enters into a separator 15 where further condensation is effected. The condensed solution is returned through pipe 16 to the upper portion of the regenerator 12. The gas remaining from the condensation, which contains $H_2S$ and some $CO_2$, is removed through pipe 17 for final disposal (e.g., to a vent or incinerator or an apparatus which converts the $H_2S$ to sulfur, such as a Claus unit or a Stretford conversion unit (not shown)).

The solution is liberated from most of the gas which it contains while flowing downward through the regenerator 12 and exits through pipe 18 at the bottom of the regenerator for transfer to a reboiler 19. Reboiler 19, equipped with an external source of heat (e.g. steam injected through pipe 20), vaporizes a portion of this solution (mainly water) to drive further $H_2S$ therefrom. The $H_2S$ and steam driven off are returned via pipe 21 to the lower section of the regenerator 12 and exited through pipe 13 for entry into the condensation stages of gas treatment. The solution remaining in the reboiler 19 is drawn through pipe 22, cooled in heat exchanger 9, and introduced via the action of pump 23 (optional if pressure is sufficiently high) through pipe 5 into the absorber column 2.

The amino compounds herein are found to be superior to those used in the past in terms of both selectivity and capacity for maintaining selectivity over a broad loading range. Typically, a gaseous stream to be treated having a 1:10 mole ratio of $H_2S:CO_2$ from an apparatus for thermal conversion of heavy residual oil, or a Lurgi coal gas having a mole ratio of $H_2S:CO_2$ of less than 1:10 will yield an acid gas having a mole ratio of $H_2S:CO_2$ of about 1:1 after treatment by the process of the present invention. The process herein may be used in conjunction with another $H_2S$ selective removal process; however, it is preferred to carry out the process of this invention by itself, since the amino compounds are extremely effective by themselves in preferential absorption of $H_2S$.

The invention is illustrated further by the following examples, which, however, are not to be taken as limiting in any respect. All parts and percentages, unless expressly stated to be otherwise, are by weight.

EXAMPLE 1

Continuous Process for the Synthesis of BTEE/EEETB Mixture

A continuous process with a fixed-bed reactor was used to synthesize the mixture of BTEE/EEETB. The catalyst was Exxon's trimetallic catalyst T-2330 (Ni/Cu/Co supported on $SiO_2$/Kieselguhr). The reaction conditions were: tertiarybutylamine/triethyleneglycol molar ratio of 3/1 (1.46/1 wt. ratio); 200° C. temperature; space velocity of 5 vol/vol/hr. 95.4% of the triethylene glycol was converted to a BTEE/EEETB mixture of composition 63/37 by weight. Purification of the crude reaction product by evaporation (without distillation) gave 60.7 wt % BTEE, 35.1 wt % EEETB, 1.6 wt % of triethyleneglycol, 0.2 wt % of tertiarybutyl morpholine, 1.6 wt % of methyltertiarybutylaminoethoxyethyl ether and 0.8% of unidentified impurities. Other BTEE/EEETB compositions are achieved by changes in reaction parameters, such as reactant molar ratio, temperature, and space velocity.

EXAMPLE 2

Batch Process for the Synthesis of BTEE/EEETB Mixtures

Example 2 demonstrates control of BTEE/EEETB compositions in batch mode synthesis via the reaction of triethyleneglycol (TEG) with tertiarybutylamine, by variation in reaction time.

| Time, hr | % TEG | % EEETB | % BTEE |
|---|---|---|---|
| 2 | 15.3 | 73 | 11.2 |
| 4 | 0 | 61.8 | 33.3 |
| 6 | 0 | 43.8 | 50.8 |
| 24 | 0 | 16.1 | 76.6 |

EXAMPLE 3

$H_2S$ Absorption by Means of BTEE/EEETB

The reaction apparatus was a 1-liter, 4-neck flask, equipped with thermometer, magnetic bar, 3-way stopcock and reflux condenser. 62 g of BTEE, 40 g of EEETB and 98 g of $H_2O$ were put into the flask, which was then evacuated and connected to an $H_2S$ bag. When no more $H_2S$ was absorbed, as indicated by a U-shaped manometer connected to the top of the reflux condenser, a sample was taken and analyzed for $H_2S$. The result was 10.4 wt %. Then the solution was refluxed for 3 hours, a sample was taken and analyzed for $H_2S$. The result was 0.04 wt %.

The experiment was repeated for comparison using a solution of 40 g of monoethanolamine in 160 ml of $H_2O$. The rich solution contained 9.55 wt % of $H_2S$. The lean solution contained 0.09 wt % of $H_2S$.

EXAMPLE 4

Selective $H_2S$ Removal from a Mixture Containing $H_2S$ and $CO_2$

FIG. 2 illustrates the sparged absorber unit, operated on a semi-batch mode, used to evaluate the selectively of $H_2S$ removal of the amino compounds of the invention herein. A gas mixture comprised of 10% $CO_2$, 1% $H_2S$ and 89% $N_2$ expressed in the volume percent, respectively, was passed from a gas cylinder (not shown) through line 30 to a meter 31 measuring the rate at which the gas is fed to the absorber. For all examples this rate was 3.6 liters per minute. The gas was then passed through line 32 to a gas chromatography column (not shown) continuously monitoring the composition of the inlet gas and through lines 33 and 34 to a sparged absorber 35, which is a cylindrical glass tube 45 cm high and 3.1 cm in diameter charged with 100 ml of the absorbent amine solution 36. The gas was passed through the solution at a solution temperature of 40° C., and about 5 ml samples of the solution were periodically removed from the bottom of the absorber unit through lines 34 and 37 to be analyzed for $H_2S$ and $CO_2$ content. The $H_2S$ content in the liquid sample was determined by titration with silver nitrate. The $CO_2$ content of the liquid sample was analyzed by acidifying the sample with an aqueous solution of 10% HCl and measuring the evolved $CO_2$ by weight gain on NaOH-coated asbestos.

While the solution was being periodically withdrawn from the bottom of the absorber unit, the gas mixture was removed from the top thereof via line 38 to a trap 39 which served to scrub out any $H_2S$ in the outlet gas. The resulting gas could optionally then be passed via lines 40 and 41 for final disposal or via line 42 to a gas chromatography column (not shown) for periodic evaluation of the composition of the outlet gas to check for system leaks. For purposes of the examples, the $H_2S$ and $CO_2$ contents of the inlet gas phase were measured and the $H_2S$ and $CO_2$ contents of the liquid phase were determined as described above. These data were used to calculate selectivity values of the amine as defined above, which were plotted as a function of the loading of the absorbent solution containing $H_2S$ and $CO_2$ in units of weight percent of $H_2S$ in solution.

In this example, an aqueous solution containing 31 wt % of BTEE and 20 wt % of EEETB was used as the absorbent solution. The selectivity plot is shown in FIG. 3 as compared to the selectivity plot for ethoxyethanol-tertiarybutylamine (EETB). As shown in this figure, BTEE/EEETB has a higher selectivity of $H_2S$ vs. $CO_2$ than EETB.

Figure 4:
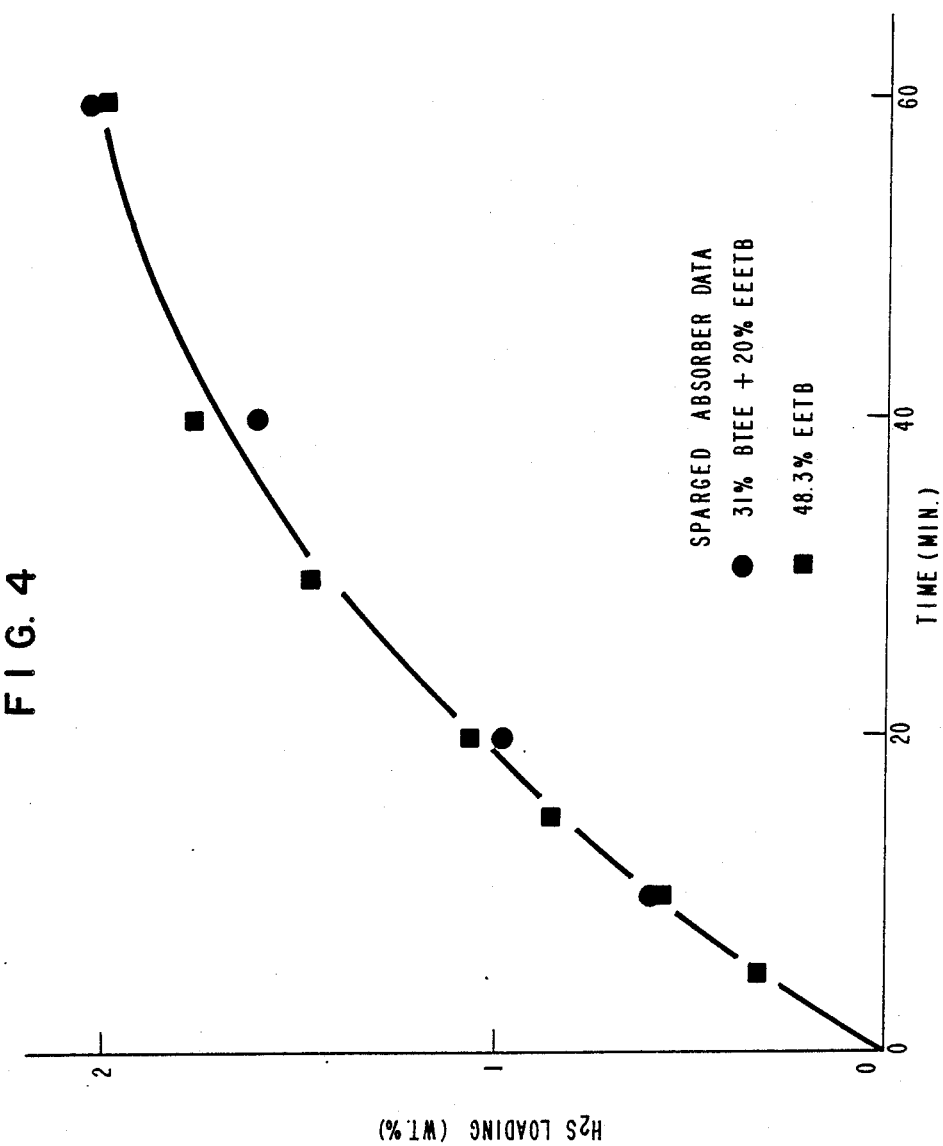
FIGS. 4 and 5 show that the higher selectivity of BTEE/EEETB as compared to EETB is due to the fact that the rate of absorption of H$_2$S is the same for the two absorbing agents, whereas the rate of absorption of CO$_2$ is lower for BTEE/EEETB.
Figure 5:
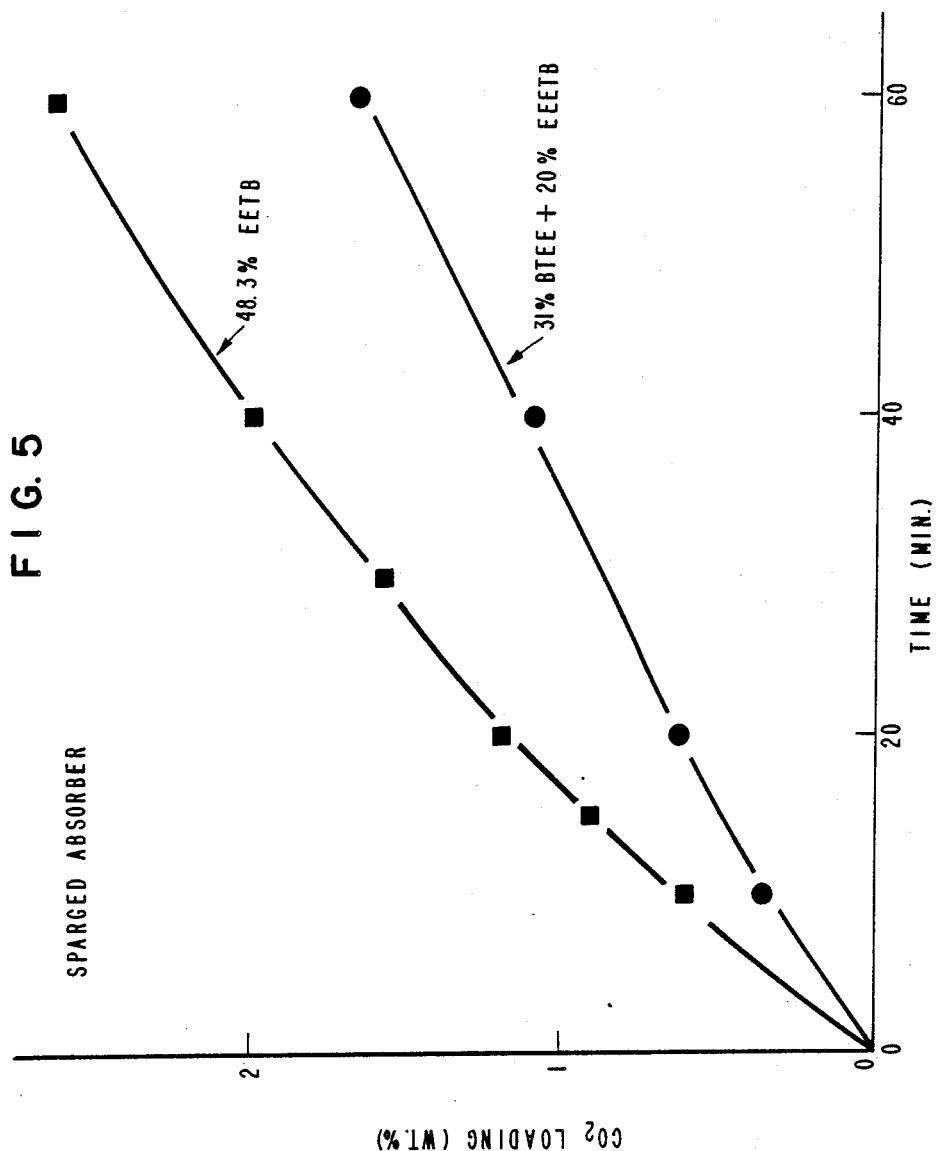

FIGS. 4 and 5 show the $H_2S$ loading and $CO_2$ loading obtained in the above experiment as a function of contacting time. The BTEE/EEETB mixture had the same $H_2S$ absorption rate as ethoxyethanol-tertiary-butylamine (EETB) but a lower $CO_2$ absorption rate leading to a higher selectivity.

EXAMPLE 5

Figure 6:
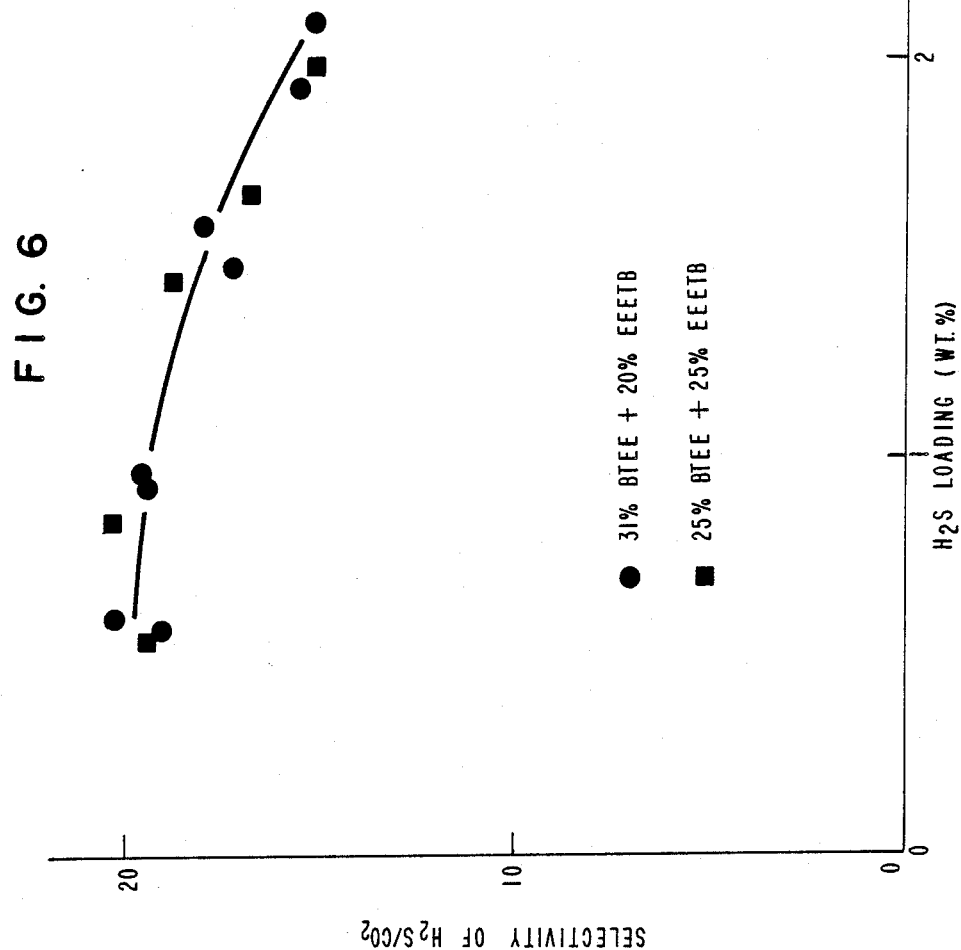
FIG. 6 shows that it is possible to vary the relative amounts of BTEE and EEETB without affecting the selectivity for H$_2$S.

Example 4 was repeated using an aqueous solution containing 25 wt % each of BTEE and EEETB. FIG. 6 shows that the selectivity as a function of $H_2S$ loading was about the same as that of 31 wt % BTEE+20 wt % EEETB.

EXAMPLE 6

Figure 7:
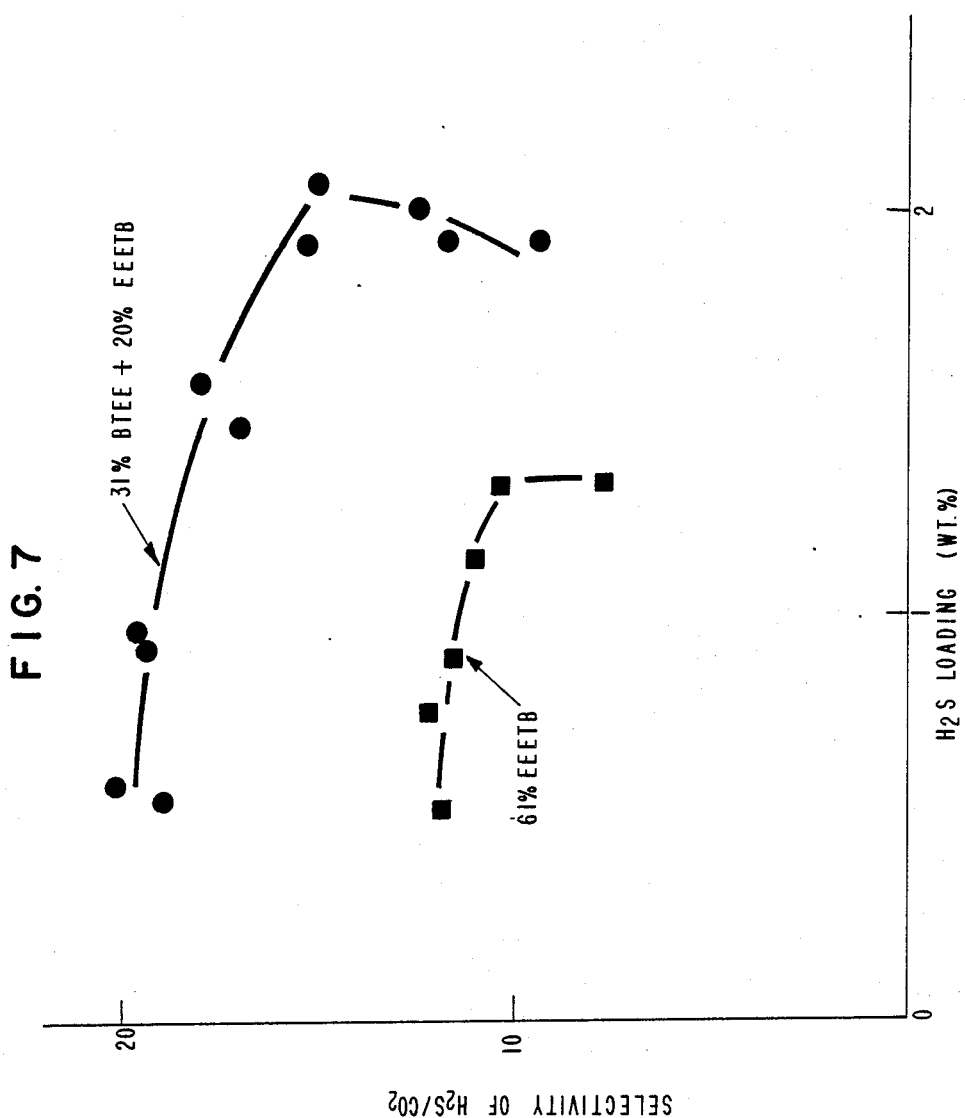
FIG. 7 shows that BTEE/EEETB has higher selectivity than EEETB.

This example shows that BTEE/EEETB has higher $H_2S$ selectivity and capacity than EEETB. Two solutions were compared by the use of the sparged absorber unit, which was the same absorption apparatus as that described in Example 4. The first solution was 31 wt % BTEE+20 wt % EEETB in water whereas the second solution was 61 wt % EEETB in water. FIG. 7 shows that the BTEE/EEETB solution had higher $H_2S$ selectivity and capacity than the EEETB solution.

EXAMPLE 7

Figure 8:
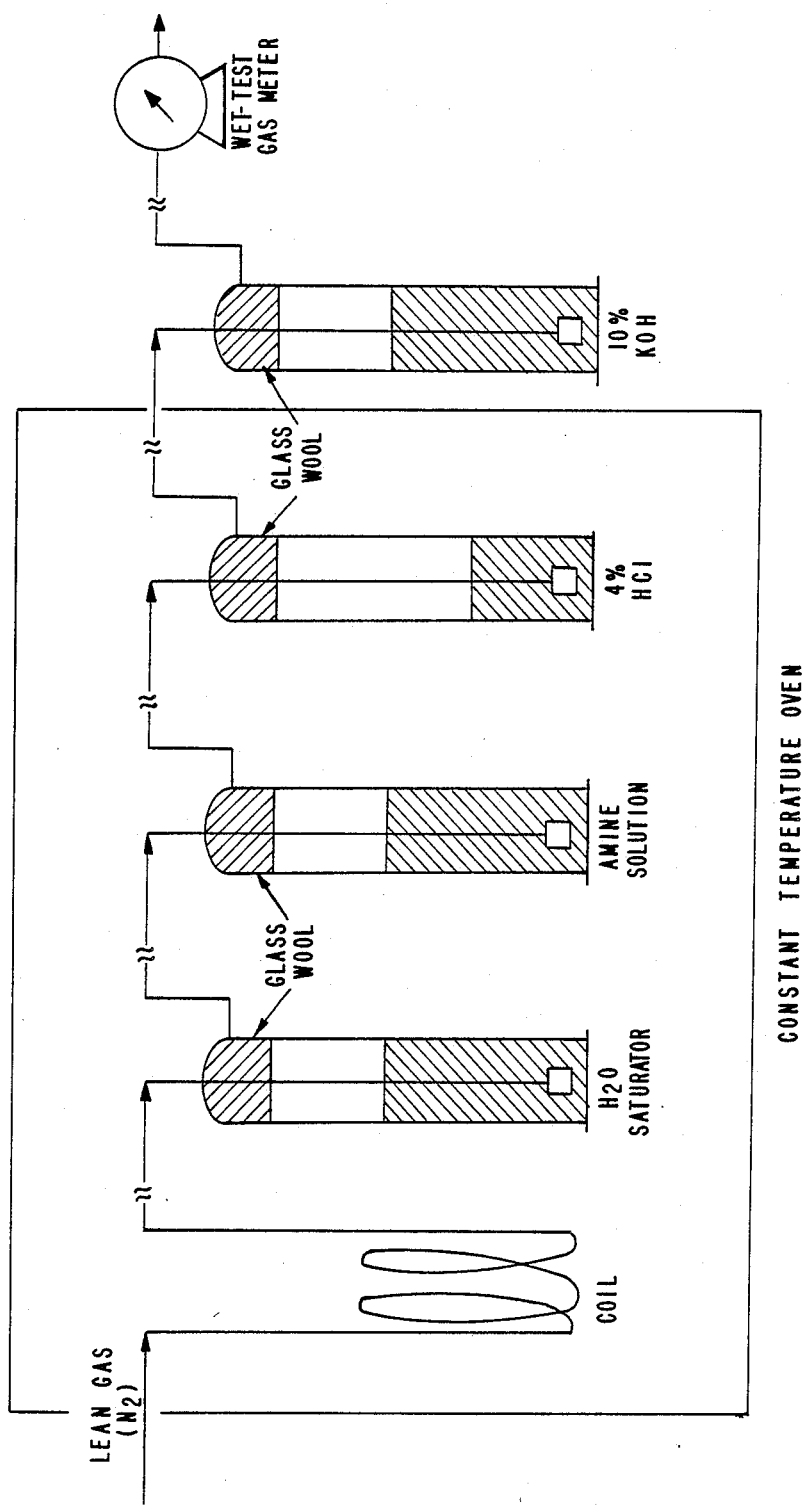
FIG. 8 shows the apparatus used for volatility tests.

This example shows that a BTEE/EEETB mixture has a lower volatility than ethoxyethanol-tertiarybutylamine (EETB). The volatility measuring apparatus is shown schematically in FIG. 8. This apparatus consisted of the following six parts in series for the flow of nitrogen gas: (1) s.s. tubing coil to equilibrate the $N_2$ gas to the set temperature, (2) $H_2O$ saturator to saturator to saturate the $N_2$ gas with water vapor, (3) bubbler containing the amine solution for testing, which saturated the $N_2$ gas with the amine, (4) bubbler containing 4% HCl solution to remove the amine from the $N_2$ gas, (5) bubbler containing 10% KOH to remove any trace HCl from the $N_2$ gas, and (6) wet-test gas meter to measure the total volume of the $N_2$ gas passing through the system for the experiment. The first four parts were in a constant temperature oven. The $N_2$ gas flow rate was 0.5 liter/min. The volatility for the amine solution was obtained from the amount of the amine trapped in the HCl solution and the volume of the $N_2$ gas measured by the wet-test meter. The amount of the amine in the HCl solution was determined by the following procedure: (1) neutralize the solution with 50% KOH to a pH value of about 6, (2) saturate the solution with $K_2CO_3$, (3) extract the aqueous phase with isopropanol, (4) separate and recover the isopropanol phase and dry it over $Na_2SO_4$, and (5) analyze the concentration of the amine in the isopropanol phase by gas chromatography. Table 1 shows the volatility results obtained with BTEE/EEETB and EETB at 40° C. The BTEE/EEETB at a total concentration of 25 wt. % (each at 12.5 wt. %) in water has much lower volatility than EETB at the same total concentration in water.

TABLE 1

| BTEE/EEETB HAS LOWER VOLATILITY THAN EETB | |
|---|---|
| Amine Concentration in Solution | Volatility at 40° C. (VPPM) |
| 12.% BTEE + 12.5% EEETB | 0.31 |
| 25% EETB | 6 |

What is claimed is:

1. An absorbent composition comprising a mixture of:
(1) a first severely hindered amine with the formula:

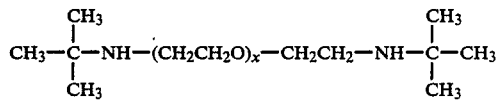

and
(2) a second severely hindered amine with the formula:

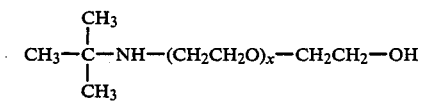

wherein said first and second severely hindered amines have a cumulative $-E_s$ value greater than 1.75, with x being an integer ranging from 2 to 6 and the weight ratio of the first amine to the second amine ranging from 0.43:1 to 2.3:1.

2. The composition of claim I wherein said first amine is:

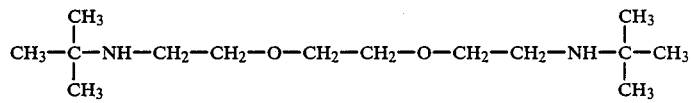

3. The composition of claim 1 wherein said second amine is:

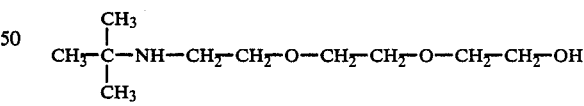

4. The composition of claim 1 wherein said absorbent composition additionally comprises a liquid selected from the group consisting of water, an organic solvent and mixtures thereof.

* * * * *